(12) United States Patent
Hanefeld et al.

(10) Patent No.: US 10,369,217 B2
(45) Date of Patent: Aug. 6, 2019

(54) ANTIGEN-LOADED CHITOSAN NANOPARTICLES FOR IMMUNOTHERAPY

(71) Applicant: MERCK PATENT GMBH, Darmstadt (DE)

(72) Inventors: Andrea Hanefeld, Darmstadt (DE); Markus Weigandt, Mannheim (DE); Michael Wolf, Darmstadt (DE); Percy Knolle, Munich (DE); Matthias Schroeder, Bonn (DE); Regina Scherliess, Kiel (DE); Peter Walden, Berlin (DE); Andrea Diedrich, Luenberg (DE); Hartwig Steckel, Kiel (DE); Renato Brito Baleeiro, Berlin (DE)

(73) Assignee: MERCK PATENT GMBH, Darmstadt (DE)

( * ) Notice: Subject to any disclaimer, the term of this patent is extended or adjusted under 35 U.S.C. 154(b) by 52 days.

(21) Appl. No.: 15/316,709

(22) PCT Filed: May 12, 2015

(86) PCT No.: PCT/EP2015/000974
§ 371 (c)(1),
(2) Date: Dec. 6, 2016

(87) PCT Pub. No.: WO2015/185180
PCT Pub. Date: Dec. 10, 2015

(65) Prior Publication Data
US 2017/0143822 A1    May 25, 2017

(30) Foreign Application Priority Data

Jun. 6, 2014 (EP) .................... 14001974

(51) Int. Cl.
| | | |
|---|---|---|
| *A61K 31/722* | (2006.01) | |
| *A61K 8/64* | (2006.01) | |
| *A61K 9/14* | (2006.01) | |
| *A61K 39/39* | (2006.01) | |
| *A61K 9/16* | (2006.01) | |
| *A61K 9/51* | (2006.01) | |
| *A61K 39/00* | (2006.01) | |

(52) U.S. Cl.
CPC ............ *A61K 39/39* (2013.01); *A61K 9/1623* (2013.01); *A61K 9/1682* (2013.01); *A61K 9/5161* (2013.01); *A61K 2039/541* (2013.01); *A61K 2039/55555* (2013.01); *A61K 2039/55583* (2013.01); *A61K 2039/6087* (2013.01)

(58) Field of Classification Search
None
See application file for complete search history.

(56) References Cited

U.S. PATENT DOCUMENTS

| 8,137,697 | B1 | 3/2012 | Sung et al. | |
|---|---|---|---|---|
| 2010/0015232 | A1* | 1/2010 | Besenbacher | A61K 9/0073 424/489 |
| 2010/0150960 | A1* | 6/2010 | Schlom | A61K 39/145 424/208.1 |
| 2011/0189299 | A1* | 8/2011 | Okubo | A61K 9/0043 424/491 |
| 2014/0065219 | A1* | 3/2014 | Bosch | A61K 9/0075 424/489 |

OTHER PUBLICATIONS

International Search Report for PCT/EP2015/000974 dated Jul. 2, 2015.
Zhang, H. et al., "Monodisperse Chitosan Nanoparticles for Mucosal Drug Delivery," Biomacromolecules, 2004, vol. 5, pp. 2461-2468.
Cui, Z. et al., "Chitosan-based nanoparticles for topical genetic immunization," Journal of Controlled Release, 2001, vol. 75, pp. 409-419.

* cited by examiner

*Primary Examiner* — Robert T. Crow
*Assistant Examiner* — John P Nguyen
(74) *Attorney, Agent, or Firm* — Millen White Zelano & Branigan

(57) ABSTRACT

The present invention is directed to nanoparticles comprising chitosan and an antigen, whereby the chitosan has a degree of deacetylation of about 90% and a molecular weight from 5 kDa to 80 kDa, to microparticles containing such nanoparticles as well as to a process for preparation of such particles. The particles are usable for vaccination.

28 Claims, 5 Drawing Sheets

ANTIGEN-LOADED CHITOSAN NANOPARTICLES FOR IMMUNOTHERAPY

The present invention is directed to nanoparticles comprising chitosan and an antigen, whereby the chitosan has a degree of deacetylation of about 90% and a molecular weight from 5 kDa to 80 kDa, to microparticles containing such nanoparticles and to a process for preparation of such particles. The particles are usable for vaccination.

Over 20 years ago, chitin derivatives, including chitosan, were found to have immunostimulatory activity. This immunostimulatory activity, along with the structural similarities between chitin derivatives and glucans, an immunoadjuvant class of natural polysaccharides, led several scientists to study the adjuvant capabilities of chitosan. Studies with chitosan and its derivatives focused on its affects on the immune response when coupled with other adjuvants.

Because of its mucoadhesive properties, chitosan has been explored as an adjuvant for mucosal vaccination. The mechanisms of vaccine enhancement by chitosan are believed to be due to both retention of vaccine in the nasal passages via mucoadhesion and opening of endothelial cell junctions for paracellular transport of vaccine (Ilium et al. 2001 *Adv Drug Dev* 51(I-3):81-96).

Adjuvant properties of chitosan have also been explored in subcutaneous vaccine formulations against infectious diseases and for cancer vaccines (In vivo evaluation of chitosan as an adjuvant in subcutaneous vaccine formulations, R. Scherließ et al., Vaccine 2013; Chitin, Chitosan, and Glycated Chitosan Regulate Immune Responses: The Novel Adjuvants for Cancer Vaccine, X. Li et al., *Clin and Dev Immunol,* 2013)

Particulate vaccines have also been described in the literature to possess adjuvant properties (e.g. Pathogen recognition and development of particulate vaccines: Does size matter?, S. Xiang, *Methods,* 2006).

US 2004/0037840 A1 (novel therapeutic vaccine formulations) discloses that immune responses against polypeptide antigens can be induced by chitosan in admixture with such polypeptide antigen and discloses microparticles as preferred formulation for this. Most preferred is that the microparticles have a mean particle diameter between 0.73 and 0.82 μm and that the chitosan has a mean molecular weight from about 95,000 to about 3,000,000 and a degree of deacetylation (DD) of at least 98%.

Notwithstanding to formulations described in the prior art there is an ongoing demand for further formulations, especially formulations providing an improved efficacy compared to existing formulation. Therefore, it was an object of the present invention to provide such formulations.

Surprisingly, it has been found by the present invention that the immune response induced by antigen containing chitosan nanoparticles is dramatically increased, if the chitosan of such nanoparticles has a degree of deacetylation (DD) of about 90% and a molecular weight from 5 kilodalton (kDa) to 80 kilodalton (kDa). Such finding is in clear contrast to the prior art teaching, which teaches that the DD value of chitosan in the particles should preferably be as high as possible (at least 98%) and that the chitosan should preferably have a mean molecular weight in a range, which is much higher than those of nanoparticles of the present invention, which have proved to provide an increased effect. Accordingly, one object of the present invention is directed to nanoparticles comprising chitosan and an antigen, which are characterized in that the chitosan has a degree of deacetylation of about 90% and a molecular weight from 5 kDa to 80 kDa.

As used herein, "a" or "an" shall mean one or more. As used herein when used in conjunction with the word "comprising," the words "a" or "an" mean one or more than one. As used herein "another" means at least a second or more. Furthermore, unless otherwise required by context, singular terms include pluralities and plural terms include the singular.

The term "nanoparticles" as used herein refers to particles having a mean size of less than 1 μm. The nanoparticles preferably have a regular shape, such as spheres, but may also have an irregular shape.

The term "microparticles" as used herein refers to particles having a mean size of more than 1 μm. The microparticles can have a regular shape, such as spheres, or an irregular shape. In an embodiment, the microparticles are built up of nanoparticles and an excipient being capable to provide sufficient cohesion of nanoparticles to form microparticles having a sufficient physical stability required for their respective use. A suitable excipient may be, for example, an excipient having adhesive properties, such as, for example a sugar or sugar alcohol.

The term "chitosan" as used herein refers to a linear polysaccharide composed of randomly distributed β-(1-4)-linked D-glucosamine (deacetylated unit) and N-acetyl-D-glucosamine (acetylated unit). Chitosan is commercially produced by deacetylation of chitin, which is a polysaccharide of N-acetyl-D-glucosamine. Different chitosans can be characterized by molecular weight, viscosity and degree of deacetylation (DD) compared to chitin.

Beside chitosan its derivatives or analogues that are capable of forming nanoparticles with an antigen can be also used for the object of the present invention. Such analogues or derivatives may be a modified chitosan, where the modification serves to alter the physical, chemical or physiological properties thereof. Such an analogue can be formed by non-covalent adherence due to electrostatic and/or hydrophilic and/or hydrophobic interactions or by covalent bonding to chitosan. Examples of analogues include, but are not limited to, chitosan modified by having bound thereto specific or nonspecific targeting ligands and/or membrane permeabilisation agents and/or endosomolytic agents and/or nuclear localization signals. Other examples are derivatized chitin or chitosan or the above mentioned analogues, i.e. O-acetylated and/or N-acetylated and/or N-trimmethylated chitosan or analogues. Anionic molecules (e.g. the adjuvant Poly (I:C) (Polyinosinic:polycytidylic acid) may be attached to the cationic N-trimethylated chitosan by electrostatic interaction. The chitosan based compounds may advantageously be crosslinked, either naturally or by means of cross-linking or gelling agents such as glutaraldehyde (Akbuga and Durmaz 1994 *Int J of Pharm* 111, 217-222; Aiedeh et al 1997 *J. Microencapsul.* 14, 567-576; Jameela, S. R. et al 1995 *Biomaterials* 16, 769-775), formaldehyde or alginate gelation (Liu, L. S. et al 1997 *J. Control Rel.* 43, 65-74; Alexakis, T. et al 1995. *Appl. Biochem. Biotechnol.* 50, 93-106; Polk A. et al 1994 *J. Pharm. Sci.* 83, 178-185).

The term "antigen" as used herein refers to all, or parts, of a protein, polypeptide, peptide or carbohydrate, capable of causing a cellular and/or humoral immune response in a vertebrate, preferably a mammal. In an embodiment, the antigen is a protein, a polypeptide, a peptide or a nucleic acid. In a further embodiment, the protein, polypeptide or peptide may be glycosylated.

The term "degree of deacetylation" (DD) as used herein refers to the percentage of free amino groups in the chitosan molecule relative to the maximum possible number of N-acetyl groups of a corresponding chitin molecule. Chitosan is most commonly prepared by alkaline deacetylation of chitin whereby acetyl groups are removed from N-acetyl-D-glucosamine units of chitin leaving behind free amino groups ($-NH_2$). Methods for the determination of the degree of deacetylation of chitosan are widely known in art and include various methods such as ninhydrin test, linear potentiometric titration, near-infrared spectroscopy, nuclear magnetic resonance spectroscopy, hydrogen bromide titrimetry, infrared spectroscopy, and first derivative UV-spectrophotometry (Khan T A, *J Pharm Pharmaceut Sci* 5(3): 205-212, 2002).

The weight-average molecular weight (Mw) was determined by static light scattering (SLS) (Scherlieβ, R., Buske, S., Young, K., Weber, B., Rades, T. and Hook, S., In vivo evaluation of chitosan as an adjuvant in subcutaneous vaccine formulations Vaccine 31 (2013) 4812-4819).

SLS is commonly used to determine the Mw of polysaccharides [Wu H. Correlations between the Rayleigh ratio and the wavelength for toluene and benzene. Chemical Physics 2010; 367: 44-7]. A laser light is sent into the sample and the scattered light is determined. The intensity of scattered light is proportional to the molecular weight (weight-average) and the concentration of polymer. This proportionality is given by the reduced Rayleigh equation [Molecular weight measurements with the Zetasizer Nano system: Malvern application note] (Equation 2)

$$\frac{KC}{R_\theta} = \left(\frac{1}{M}\right) + 2A_2 C$$

Equation 2: Rayleigh equitation, where K is an optical constant, $R_\theta$ is the Rayleigh ratio, M is the weight-average molecular weight, $A_2$ is the second virial coefficient and C is the sample concentration.

Using the Rayleigh equation in a Debye plot, a linear fit of KC/R versus C can be generated where the intercept is equal to the inverse molecular weight and the resulting slope is twice the second virial coefficient. To determine the molecular weight, static light scattering measurements are performed using a ZetaSizer Nano ZS (Malvern Inc., Malvern, UK). The ZetaSizer Nano ZS is a single angle laser light scattering apparatus with an angle of 173 Degree and a He—Ne laser (633 nm) as light source. Prior to every sample measurement, background light intensity is determined and the backscattering of toluene as scattering standard with a Rayleigh ratio value of $1.35 \times 10-5$ $cm^{-1}$ is measured. Samples are dissolved in 0.02 M sodium acetate and 0.1 M sodium chloride at a pH-value of 4.5 and a refraction index increment (dn/dc) of 0.192 mL/g is assumed (Nguyen S, Hisiger S, Jolicoeur M, Winnik F M, Buschmann M D. Fractionation and characterization of chitosan by analytical SEC and 1H NMR after semi-preparative SEC. Carbohydrate Polymers 2009; 75: 636-45). Five different sample concentrations in the range from 0.25 to 1.00 g/L are prepared and measured. Prior to each measurement samples are filtered through a 0.45 m PTFE filter into a square glass cuvette. Measurements are performed at a temperature of 20° C., and data are analysed via the Debye plot method.

As used herein, "about" refers to a numeric value, including, for example, whole numbers, fractions, and percentages, whether or not explicitly indicated. The term "about" generally refers to a range of numerical values (e.g., +/-1-3% of the recited value) that one of ordinary skill in the art would consider equivalent to the recited value (e.g., having the same function or result). In some instances, the term "about" may include numerical values that are rounded to the nearest significant figure.

Advantageously, the chitosan being present in the nanoparticles has a molecular weight from 10 kDa to 80 kDa, preferably from 20 kDa to 60 kDa and more preferably from 25 kDa to 50 kDa. Accordingly, one embodiment of the invention is directed to nanoparticles, which are characterized in that the chitosan has a molecular weight from 10 kDa to 70 kDa, preferably from 20 kDa to 60 kDa and more preferably from 25 kDa to 50 kDa.

From US 2004/0037840 A1, which discloses chitosan particles for therapeutic vaccine formulations, it is known that the vaccine particles should most preferably have a particle diameter in the range between 0.73 and 0.82 μm (see above). By contrast, it has been found by the present invention that that chitosan nanoparticles exhibit a strong and superior immunological effect if they have a mean size from 100 to 500 nm. Such immunological effect is increased, if the nanoparticles have a mean particle size from 200 nm to 400 nm, especially from 200 nm to 300 nm. Accordingly, one further embodiment of the invention is directed to nanoparticles, which are characterized in that nanoparticles have a mean size from 100 to 500 nm, preferably from 200 to 400 nm and more preferred from 200 nm to 300 nm.

The term "mean size" as used herein refers to the hydrodynamic average diameter ("z-average") of the nanoparticle population that moves together in an aqueous medium. The z-average is defined by ISO 22412 as the 'harmonic intensity averaged particle diameter'. To compare z-average sizes measured by different techniques the samples have to be monomodal (i.e. only one peak), spherical or near-spherical in shape and monodisperse (i.e. very narrow width of distribution). The mean size of these systems can be measured by standard processes known by the person skilled in the art, and which are described, for example, in the experimental part (see below).

Advantageously, the nanoparticles of the present invention contain a counterion. Therefore, a preferred embodiment of the invention is directed to nanoparticles, which are characterized in that they contain a counterion.

The term "counterion" as used herein refers to an anion or an anionic group derived from an organic or mineral acid salt which counterbalances the positive charge of the chitosan derived by its protonized amino groups. Counterions usable for the present invention can be divided into two major categories: low molecular weight counterions such as chloride (which may be employed by using e.g. $CaCl_2$, $BaCl_2$, $MgCl_2$, $CuCl_2$, $ZnCl_2$, $CoCl_2$), $NaSO_4$, pyrophosphate, tripolyphosphate, tetrapolyphosphate, octapolyphosphate, hexametaphosphate and $[Fe(CN)_6]^{-4}/[Fe(CN)_6]^{-3}$ and high molecular weight ions such as octyl sulphate, lauryl sulphate, hexadecyl sulphate, cetylstearyl sulphate, sodium cholate, carboxymethylcellulose or poly(acrylic acid)).

In a preferred embodiment of the invention the nanoparticles contain carboxymethylcellulose, pentasodium tripolyphosphate, sodium cholate heparin, low MW hyaluronic acid, alginate, pectin, carrageenan, nucleic acids (e.g. RNA or DNA) or poly(acrylic acid) as counterion. Accordingly, the invention is further directed to nanoparticles, which are characterized in that the counterion is carboxymethylcellulose, pentasodium tripolyphosphate, sodium cholate heparin, hyaluronic acid, alginate, pectin, carrageenan, nucleic acids (e.g. RNA, DNA or RNA-based RIG-I-like ((retinoic acid inducible gene I)-like) receptor agonists) or poly(acrylic acid).

The nanoparticles advantageously contain a peptide, a polypeptide or a protein as antigen. Therefore a preferred embodiment of the invention is directed to nanoparticles, which are characterized in that the antigen is a peptide, a protein or a nucleic acid.

The term "peptide" as used herein refers to a chain of at least two amino acids attached to one another by a peptide bond. In some embodiments, a peptide may include at least 3-5 amino acids, each of which is attached to others by way of at least one peptide bond. The term "peptide" sometimes includes "non-natural" amino acids or other entities that nonetheless are capable of integrating into a polypeptide chain. The term "peptide" embraces the term "polypeptide", which as used herein, refers to a long, continuous, and unbranched peptide chain containing about 10 to about 100 amino acids or more.

The term "protein" as used herein refers to a macromolecule containing more than 100 amino acids attached to one another by a peptide bond. Proteins contain one or more polypeptides, for example linked by one or more disulfide bonds or associated by other means, and may include moieties other than amino acids (e.g., may be glycoproteins, proteoglycans, etc.) and/or may be otherwise processed or modified. A "protein" can be a complete polypeptide chain as produced by a cell (with or without a signal sequence), or can be a characteristic portion thereof.

Peptides, polypeptides and proteins may contain l-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof.

The term "nucleic acid" as used herein refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

If a nucleic acid is present as an antigen it may (due to its negative charge) counterbalance the positive charge of the chitosan derived by its protonized amino groups. In such instances the nucleic acid acts itself as a counterion as described above so that no further counterion is necessary or is needed in a reduced amount only.

Notwithstanding to the adjuvant effect of the chitosan, in one embodiment of the invention the nanoparticles may further contain an adjuvant.

The term "adjuvant" as used herein refers to any substance which is capable of enhancing the immune response against an antigen. If combined with an antigen an adjuvant such combination induces an immune response against the antigen, which is stronger than that induced by the antigen alone. Examples of usable adjuvants are CpG, CTB, c-di-AMP, Poly IC, RNA-based RIG-I receptor agonists, or cytokines.

The nanoparticles can be used for vaccination including preventive and therapeutic vaccination. Therefore, the invention is also directed to nanoparticles for use of vaccination. Specific embodiments of the invention are nanoparticles for use as therapeutic vaccine as well as to nanoparticles for use as preventive vaccine. The use of the nanoparticles for therapeutic vaccination is especially preferred.

As used herein, the term "vaccine" as used herein refers to a therapeutic or prophylactic pharmaceutical formulation that contains a component against which a vaccinated host is induced to raise an immune response, preferably a protective immune response. Preferably, such a component that induces an immune response is an antigen.

The term "therapeutic" together with "vaccine" as used herein refers to that the immune response induced by the vaccine treats, ameliorates or lessens an ongoing disease, such as, for instance, cancer, after its onset or detection. The term "therapeutic vaccination" as used herein refers to the use of a therapeutic vaccine for treatment, amelioration or lessening an ongoing disease, such as AIDS, tuberculosis, autoimmune diseases (e.g. multiple sclerosis and rheumatoid arthritis), gastric ulcers or cancer.

The term "preventive" together with "vaccine" as used herein refers to that the immune response is induced by the vaccine in an uninfected subject to provide protection against a disease induced by microbial or viral infection or to reduce the severity of the microbial invasion. The term "preventive vaccination" as used herein refers to the use of a preventive vaccine for inducing an immune response in an uninfected subject to provide protection against a disease induced by microbial or viral infection or to reduce the severity of the microbial invasion.

According to a particularly preferred embodiment of the present invention the nanoparticles are for use of therapeutic vaccination, preferably for cancer vaccination. Likewise the present invention is also directed to the use of nanoparticles for therapeutic vaccination, preferably for cancer vaccination and vaccination for autoimmune diseases In case of cancer vaccination the nanoparticles must contain an appropriate tumor antigen. Nanoparticles for cancer vaccination must (i) include peptide sequences that bind to major histocompatibility complex (MHC) class I, (ii) be processed by tumor cells and become available for binding to MHC I molecules, (iii) be recognised by the T cell repertoire in an MHC I—restricted fashion, and (iv) drive the expansion of cytotoxic T lymphocyte (CTL) precursors expressing specific T cell receptors (Matera L, *Cancer Treat Rev* 36(2): 131-141, 2010).

Since the molecular cloning of the first gene reported to encode a CTL-defined human tumor antigen MAGE (Melanoma-associated antigen), and with the development of new technologies, many other antigens recognized by T cells on human cancers, the so-called tumor associated antigens (TAA), have been identified and characterized (Van der Bruggen et al., *J Immunol* 178(5): 2617-2621, 2007; Novellino L et al., *Cancer Immunol Immunother* 54(3): 187-207, 2005). Other examples of TAAs are CEA (Carcinoembryonic antigen), CA-125 (Cancer antigen 125), MUC-1 (Mucin 1), ETA (Epithelial tumor antigen) and CTAG1B (Cancer/testis antigen 1b).

The nanoparticles of the present invention can be administered by various routes such as via mucosal or parenteral route, such as subcutaneous, intramuscular, intraperitoneal and intravenous route. As used herein, the term "mucosal" refers to any membrane surface of the body covered by mucous, such as the nasal, pulmonary, oral (sublingual, buccal), gastroenteric, rectal, urinary, conjunctial, glandular, e.g. mammary gland, epithelial mucous. Accordingly, one embodiment of the invention is directed to the use of the nanoparticles for vaccination which is characterized in that the nanoparticles are administrated by mucosal administration or by parenteral injection. Preferably, the nanoparticles are administered by mucosal route, whereby the nasal and pulmonary route is especially preferred. Therefore, one preferred embodiment is directed to the use of the nanoparticles for vaccination which characterized in that the mucosal administration is pulmonal or nasal administration.

Mucosal administration of the nanoparticles can be performed using liquid dispersions and devices known in the art. Delivery of the liquid nanoparticle dispersion can be performed with controlled particle size ranges, which are adapted to the specific route of administration, by using devices known in the art. For example, the nanoparticles dispersion can be administrated to the nasal mucosa by using mechanical pumps or sprayers. Delivery to the pulmonal mucosa can be achieved, for example, by nebulization of the nanoparticle dispersion to the lungs using commercially available pressurized metered dose inhalers (pMDIs). Preferably the liquid dispersions used for administration of the nanoparticles to the mucosa are aqueous dispersions wherein the nanoparticles are dispersed in an aqueous solution.

Chitosan nanoparticles can be prepared by various methods which are known by a person skilled in the art such as ionic gelation method, emulsification and cross-linking, emulsion droplet coalescence, emulsion solvent diffusion, reverse micellisation, ionic gelation, polyelectrolyte complexation, modified ionic gelation with radical polymerization, desolvation (*A. Grenha, Chitosan nanoparticles: a survey of preparation methods, J Drug Targeting,* 2012). Ionic gelation method is preferred as it is very simple and mild and as it involves reversible physical crosslinking by electrostatic interaction instead of chemical crosslinking, which avoids the possible toxicity of reagents and other undesirable effects. Advantageously, the nanoparticles can be prepared under mild conditions without using harmful solvents, especially organic solvents, which may cause degradation of the antigen as it may be the case if it is a peptide or protein antigen that is unstable and sensitive to other process environments.

The term "ionic gelation", as used herein, refers to complexation between oppositely charged molecules to prepare nanoparticles. In an embodiment of the ionic gelation method chitosan is dissolved in an aqueous medium, which is preferably weak acidic to foster conversion of free amino acid groups ($-NH_2$) to its positively charged protonized form ($-NH_3^+$). Such solution is then combined with an aqueous solution containing negatively charged counterions, for example by addition of an aqueous solution containing chitosan to an aqueous solution containing negatively charged counterions or vice versa. Preferably, the combination of aqueous solutions is done by dropwise addition of one aqueous solution to the other under constant stirring. Due to the complexation between oppositely charged species, chitosan undergo ionic gelation and precipitate to form spherical particles. The nanoparticles can be removed by filtration, washed with distilled water and dried. Accordingly, a preferred embodiment of the invention is directed to a process for the preparation of the nanoparticles, which is characterized in that the nanoparticles are prepared by ionic gelation.

The term "aqueous solution", as used herein, refers to any solution or suspension, wherein at least some of the solvent present consists of water. Further solvent constituents that may be present are alcohols, such as, for example, ethanol, propanol, propanediol or glycerol. The aqueous solution preferably comprises water or a ethanol/water mixture as solvent, the solvent particularly preferably consists of water. In certain embodiments the aqueous solution comprises a pH modifying agent, such as an acid, a base or a buffer substance. In a preferred embodiment the aqueous solution contains an agent that provide a weak acidic pH, such as acetic acid/acetate buffer.

An appropriate process for preparation of the nanoparticles comprises the steps (a) preparing an aqueous solution comprising chitosan and an antigen; (b) preparing an aqueous solution comprising a counterion; (c) mixing the aqueous solution prepared in step (a) and the aqueous solution prepared by step (b); (d) stirring the mixture obtained in step (c) to produce an aqueous dispersion containing chitosan nanoparticles; (e) collecting the nanoparticles obtained in step (d).

Therefore, the invention is also directed to a process for the preparation of the nanoparticles, which comprises the steps:

(a) preparing an aqueous solution comprising chitosan and an antigen;
(b) preparing an aqueous solution comprising a counterion;
(c) mixing the aqueous solution prepared in step (a) and the aqueous solution prepared by step (b);
(d) stirring the mixture obtained in step (c) to produce an aqueous dispersion containing chitosan nanoparticles;
(e) collecting the nanoparticles obtained in step (d).

According to an alternative embodiment of the process the antigen is present in the aqueous solution comprising the counterion (step (b)) instead of the aqueous solution comprising chitosan (sep (a)). According to a further alternative embodiment of the process the antigen is present in both aqueous solutions, i.e. in the aqueous solution comprising chitosan (step (a)) and in the aqueous solution comprising the counterion (step (b)).

Preferably, the mixing of aqueous solutions in step (c) of such process is performed by addition of the aqueous solution prepared in step (b) to the aqueous solution prepared by step (a). Accordingly, the invention is also directed to a process of preparation of nanoparticles, wherein step (c) is performed by addition of the aqueous solution prepared in step (b) to the aqueous solution prepared by step (a).

As described above the nanoparticles of the present invention can advantageously be used for vaccination, whereby mucosal administration, especially pulmonal and nasal administration, is a preferred administration route. Due to their small particle size such nanoparticles may not directly be administrated in an appropriate way and require to be dispersed in a liquid medium, especially an aqueous medium, which may have a detrimental effect on the stability of the nanoparticles during storage. For example, direct pulmonal administration of the very small nanoparticles without a liquid medium providing an appropriate particle size results in their exhalation so that no immune response of the pulmonal mucosa is induced. Dry particle formulations containing the nanoparticles, which have a particle size that is usable for direct administration, are highly desired. After being administered to and upon contact with the mucosa the particles advantageously shall set free the nanoparticles, for example by their disintegration.

Therefore, it is a further object of the present invention to provide particles comprising the nanoparticles of this invention. Such particles are provided by microparticles comprising the nanoparticles of the present invention and a matrix agent.

The term "matrix agent", as used herein, refers to an agent or chemical compound that is at least partially soluble in water and aqueous media as they are present at mucosa, such as alveolar and nasal mucosa, and that can provide matrix and/or adherence of the nanoparticles to one another to form larger particles. In the microparticles formed with the matrix agent the nanoparticles may be arranged as agglomerates and/or may be completely and/or partly surrounded by the matrix agent. Upon contact of the microparticles with water or aqueous media the matrix material partially or totally dissolves in such media leading to disintegration of the microparticles and release of the nanoparticles contained therein.

Preferred matrix agents are monosaccharides, disaccharides, sugar alcohols or polysaccharides. Accordingly, one embodiment of the present invention is directed to microparticles, which are characterized in that the matrix agent is a monosaccharide, a disaccharide, a sugar alcohol or a polysaccharide.

Particularly preferred matrix agents are the monosaccharide glucose, the disaccharides trehalose, sucrose and lactose, the sugar alcohols mannitol and sorbitol, and the polysaccharides starch and dextrane. Therefore, the invention is further directed to microparticles comprising the nanoparticles, which is characterized in that characterized in that the matrix agent monosaccharide is glucose, the matrix agent disaccharide is trehalose, sucrose or lactose, the matrix agent sugar alcohol is mannitol or sorbitol, and the matrix agent polysaccharide is starch or dextrane.

In pulmonary administration, the size of the active particles is of great importance in determining the site of the absorption. In order to achieve that the particles are carried deep into the lungs, the particles must have a particular size, for example should have a mass median aerodynamic diameter (MMAD) of less than 10 μm. Particles having a MMAD greater than 10 μm are likely to impact the walls of the throat and generally do not reach the lung. It can generally be considered that particles with an MMAD higher than 10 μm are deposited in the oropharynx, those measuring between 5 and 10 μm in the central airways and those from 0.5 to 5 μm in the small airways and alveoli. Therefore, for respiratory treatment (inhalation) it is preferred to use particles with an MMAD between 0.5 and 5 μm.

The term "mass median aerodynamic diameter" (abbreviated as MMAD), as used herein, is a measure of the aerodynamic size of a dispersed particle. The MMAD distribution defines the manner in which an aerosol deposits during inhalation, and is the median diameter of a unit density particle having the same settling velocity, generally in air, as the particle. MMAD encompasses particle shape, density and physical size of a particle and refers to the midpoint or median of the aerodynamic particle size distribution of an aerosolized powder determined by Anderson cascade impaction or Next Generation Impactor (NGI). In our studies Model 170 Next Generation Pharmaceutical Impactor (NGI) was used, which is a high-performance, precision, particle-classifying cascade impactor for testing metered-dose, dry-powder, and similar inhaler devices. MSP Corporation developed this impactor in conjunction with a 15-member consortium of pharmaceutical companies (Next Generation Impactor Consortium). Substantial user-involvement in the design process has resulted in a combination of aerodynamic design principles and user-friendly operation. A removable set of collection cups minimizes the time between inhaler tests.

Other time-saving features include the absence of a final filter and of inlet O-rings. The NGI has been tested by 15 pharmaceutical companies in the Next Generation Impactor Consortium.

One embodiment of the invention refer to microparticles having a MMAD from 0.5 μm to 8 μm, preferably from 0.5 μm to 5 μm, more preferably from 1 μm to 5 μm and most preferably from 2 μm to 5 μm. Accordingly, the invention is also directed to microparticles, which are characterized in that they have a mass median aerodynamic diameter from 0.5 μm to 5 μm, preferably from 1 μm to 5 μm and more preferably from 2 μm to 5 μm.

The microparticles can be used for vaccination. Therefore, one embodiment of the invention is directed to nanoparticles for use in vaccination.

According to a preferred embodiment of the present invention the microparticles are for use in therapeutic vaccination, preferably for cancer vaccination. Likewise the present invention is also directed to the use of microparticles for therapeutic vaccination, preferably for cancer vaccination.

Beside the further various administration routes as described above for the nanoparticles the microparticles are preferably administrated by mucosal administration, more preferably by pulmonal or nasal administration, whereby pulmonal administration is most preferred. Therefore, one preferred embodiment is directed to the use of the microparticles for therapeutic vaccination which is characterized in that the mucosal administration is pulmonal or nasal administration.

For mucosal administration the microparticles can be administrated, for example, by using commercially available devices such as pressurized metered dose inhalers (pMDIs) or dry powder inhalers (DPI's). If administrated to pulmonal mucosa dry powder inhalers are preferred. Commercially available DPI's are, for example, PUFFHALER (Aktiv-Dry LLC), TWINCAPS (Hovione LLC), TORUS DPI (Manta Devices LLC) the CONIX ONE (3M) and DIRECTHALER PULMONARY (Direct-Haler A/S), CYCLOHALER (PB Pharma GmbH).

The microparticles can be prepared by using spray-drying technique. The term "spray-drying", as used herein, refers to a method of producing a dry powder comprising micron-sized particles from a solution or suspension by using a spray-dryer. Spray-drying is, in principle, a solvent extraction process. The constituents of the product to be obtained are dissolved/dispersed in a liquid and then fed, for example by using a peristaltic pump, to an atomiser of a spray-dryer. A suitable atomizer which can be used for atomization of the liquid, include nozzles or rotary discs. With nozzles, atomization occurs due to the action of the compressed gas, while in case of using rotary discs atomization occurs due to the rapid rotation of the disc. In both cases, atomization leads to disruption of the liquid into small droplets into the drying chamber, wherein the solvent is extracted from the aerosol droplets and is discharged out, for example through an exhaust tube to a solvent trap.

Drop sizes from 10 to 500 μm can be generated by spray-drying. As the solvent (water or organic solvent) dries, the nanoparticles-containing droplets dries into a micron-sized particle, forming powder-like particles.

A number of commercially available spray drying machines can be used to prepare the microparticles of the invention, for example, suitable machines are manufactured by Buchi and Niro. Examples of suitable spray-driers include lab scale spray-dryers from Buchi, such as the MINI SPRAY DRYER 290, or a MOBILE MINORTM™, or a Pharma Spray Dryer PharmaSD® from Niro, or a from Procept NV.

In a typical spray drying machine the suspension to be dried is pumped from a stirred reservoir to an atomization chamber where it is sprayed from a nozzle as fine droplets (preferably the droplets are in the range of 1 to 20 μm in diameter) into a stream of heated air, for example, inlet temperatures in the range of 50 to 150° C. (nitrogen can be used in place of air if there is a risk of undesirable oxidation of the antigen). The temperature of the heated air must be sufficient to evaporate the liquid and dry the microparticles to a free flowing powder but should not be so high as to degrade the active substance. The microparticles may be collected in a cyclone or a filter or a combination of cyclones and filters.

Suitable spray-drying techniques, which can be used for preparation of the microparticles, are well known and described, for example, by K. Masters in "Spray-drying Handbook", John Wiley & Sons, New York, 1984. In a preferred embodiment, atomization of the liquid is performed by using a nozzle.

In accordance to an appropriate embodiment of the invention, a liquid containing the nanoparticles of the present invention and the matrix agent is spray-dried. Therefore, one object of the invention is directed to a process for the preparation of microparticles, which is characterized in that a liquid containing the nanoparticles and the matrix agent is spray-dried. The liquid preferably is an aqueous solution, in which the matrix agent is dissolved and the nanoparticles are dispersed.

Preferably the process comprises the steps (a) preparing an aqueous dispersion comprising the antigen-loaded nanoparticles and the matrix building agent being dissolved therein; (b) spray-drying the aqueous dispersion prepared in step (a) to produce antigen-loaded nanoparticle-containing microparticles and (c) collecting the microparticles obtained in step (b). Therefore, the invention is also directed to a process, which is characterized in that it comprises the steps (a) preparing an aqueous dispersion comprising the antigen-loaded nanoparticles and the matrix building agent being dissolved therein;

(b) spray-drying the aqueous dispersion prepared in step (a) to produce antigen-loaded nanoparticle-containing microparticles and (c) collecting the microparticles obtained in step (b).

The term "antigen-loaded" together with "nanoparticles" refers to nanoparticles comprising an antigen as described and/or claimed by the present invention.

If the microparticles are intended to be administrated by using dry powder inhalers a particulate excipient material may be admixed to the microparticles to improve the flow of the powder. Such particles of excipient material may be coarse, for example having a mass median aerodynamic diameter greater than 90 µm (such coarse particles are referred to as carrier particles) or they may be fine.

The examples explain the invention without being restricted thereto.

Particle Size Analysis of Nanoparticles

Particle size and zeta potential measurements are performed using a Zetasizer (Malvern Instruments) applying dynamic light scattering (DLS). For data analysis the 'general purpose" analysis mode is used based on the following parameters:

Viscosity: 1.01 mPas (at 22° C.)
Refraction index: 1.328

Each sample is equilibrated to 22° C. within 120 seconds and analysis is performed in triplicate.

Zeta potential measurements are performed using specific cells. Measurements are performed in triplicate as well, using 10-100 runs (automatical adjustment). Data analysis is based on the Smoluchowski model.

Particle size analysis of microparticles

The particles size distribution of the spray-dried product is performed using a HELOS laser diffractor (Sympatec GmbH, Clausthal, Zellerfeld, Germany). Spray-dried powder is dispersed using 3 bar and measured using the HELOS Rodus module.

The capsule-based inhaler, Cyclohaler ® is used for aerodynamical characterization. Measurements are performed using the HELOS inhaler module. An air flow rate of 100l/min (=4 kPa differential pressure drop across the inhaler) is used to release the powder from the inhaler. Particle size distribution is determined by laser diffraction. HPMC capsules (size 3) filled with 10mg of spray-dried powder are dispersed using the inhaler. X50, the powder fraction <5.25 µm as well as the relative deagglomeration are determined.

Preparation of Nanoparticles (General Description)

Nanoparticles are manufactured by ionic gelation. Nanoparticles are formed spontaneously by ionic crosslinking by electrostatic interaction of the positively charged primary amino groups of chitosan with the negatively charged carboxy groups of the cellulose derivate.

For the preparation of a chitosan solution an accurate amount of chitosan (Chitoscience, Heppe Medical Chitosan), e.g. 0.1%, is dissolved in an acidic acid solution, e.g. 2%. The carboxymethylcellulose solution is prepared by dissolving an accurate amount of Tylose C30 (Hoechst), e.g. 0.1%, in purified water and added slowly to the chitosan phase while stirring on a magnetic stirrer. The resulting nanoparticles (with the chitosan/acidic acid/Tylose ratios 0.1/2 and 0.1%) have a mean size of 230 nm and a polydispersity index (PDI) of 0,140 (measured by Zetasizer Nano ZS, Malvern Instruments). Nanoparticles are sampled by centrifugation and resuspended in 1% acetic acid. Formulations containing different counter ions (e.g. examples with heparin, hyaluronic acid and polyacrylate) are prepared accordingly, the counter ions are dissolved in purified water.

The composition of the final nanoparticle suspension is as follows:

| Excipient | Parts |
|---|---|
| Chitosan | 0.05 |
| Carboxymethylcellulose | 0.05 |
| Acidic acid 99% | 1 |
| Purified water | 99.99 |
| Chitosan | 0.01 |
| Carboxymethylcellulose | 0.01 |
| Acidic acid 99% | 1 |
| Purified water | 98.98 |
| Chitosan | 0.1 |
| Carboxymethylcellulose | 0.1 |
| Acidic acid 99% | 1 |
| Purified water | 98.8 |
| Chitosan | 0.25 |
| Carboxymethylcellulose | 0.25 |
| Acidic acid 99% | 1 |
| Purified water | 98.5 |
| Chitosan | 0.25 |
| Carboxymethylcellulose | 0.25 |
| Acidic acid 99% | 2.5 |
| Purified water | 97.0 |
| Chitosan | 0.25 |
| Carboxymethylcellulose | 0.25 |
| Acidic acid 99% | 1 |
| Purified water | 98.5 |
| Chitosan | 0.01 |
| Carboxymethylcellulose | 0.01 |
| Hydrochloric acid 37% | 0.01 |
| Purified water | 99.97 |
| Chitosan | 0.25 |
| Carboxymethylcellulose | 0.25 |
| Hydrochloric acid 37% | 0.3 |
| Purified water | 99.2 |
| Chitosan | 0.05 |
| Carboxymethylcellulose | 0.05 |
| Hydrochloric acid 37% | 0.02 |
| Purified water | 99.88 |

-continued

| Excipient | Parts |
| --- | --- |
| Chitosan | 0.1 |
| Pyrophosphate | 0.3 |
| Acidic acid 99% | 1 |
| Purified water | 98.6 |
| Chitosan | 0.1 |
| Heparin | 0.1 |
| Acidic acid 99% | 1 |
| Purified water | 98.8 |
| Chitosan | 0.05 |
| Heparin | 0.05 |
| Acidic acid 99% | 1 |
| Purified water | 98.9 |
| Chitosan | 0.25 |
| Hyaluronic acid | 0.1 |
| Acidic acid 99% | 0.1 |
| Purified water | 99.55 |
| Chitosan | 0.25 |
| Hyaluronic acid | 0.05 |
| Acidic acid 99% | 0.1 |
| Purified water | 99.6 |
| Chitosan | 0.02 |
| Polyacrylic acid | 0.02 |
| Acidic acid 99% | 0.1 |
| Purified water | 99.86 |

Ovalbumin-loaded Nanoparticles are produced as follows. 0.1% (w/V) chitosan (Heppe Medical Chitosan GmbH, Germany) is dissolved with 1 mg/ml ovalbumin (OVA; Sigma, USA) in 2% (V/V) acetic acid.

0.1% (w/V) of a negatively charged cellulose derivative (TYLOSE C30 Hoechst, Germany) as agent for ionic gelation is dissolved separately in double distilled water of the same volume and added slowly to the chitosan phase while stirring. Alternatively Ovalbumin-loaded Nanoparticles are produced as follows. 0.1% (w/V) chitosan (Heppe Medical Chitosan GmbH, Germany) is dissolved (OVA; Sigma, USA) in 2% (V/V) acetic acid. 0.1% (w/V) of a negatively charged cellulose derivative (TYLOSE C30, Hoechst, Germany) as agent for ionic gelation is dissolved with 1mg/ml ovalbumin separately in double distilled water of the same volume and added slowly to the chitosan phase while stirring. Ovalbumin can also be dissolved in the TYLOSE phase following the process mentioned above. The optimal ratio of chitosan to Tylose is determined to be 1:1. TYLOSE solution needs to be added to the Chitosan solution to achieve the desired particle size.

Influence of Particle Size on their Uptake by Antigen Presenting Cells (Macrophages and Dendritic Cells)

Macrophages and dendritic cells used in this study are isolated from bone marrow of C57BL/6j mice (For isolation protocol see Schroder M. et al., Mol Immunol. 2011, 48(9-10): 1139-48). Briefly bone marrow cells are isolated from the hind legs of the mice and cultured in RPMI medium supplemented with 10% FCS, 100 IU/ml penicillin, 100 µg/ml streptomycin, 50 µM β-mercaptoethanol and either 100 nM M-CSF or 100 nM GM-CSF, for macrophage or dendritic cell differentiation respectively, in a humidified incubator (5% CO2 and 37° C.) at a cell concentration of $0.8 \times 10^6$ cells/ml in an untreated petri dish. For the differentiation process supernatant of the cell line R1 is used to either produce GM-CSF or M-CSF containing supernatants and the concentration is measured with ELISA prior to use in the experiments. After four days the cells are splitted 1:2 on additional petri dishes and cultivated for additional three days with freshly added culture medium and growth factors. After another three days the adherent cells are used for the in vitro experiments, FACS analysis and microscopic experiments. For the NP-uptake studies $5 \times 10^4$ macrophages are seeded in a 96-well cell-culture-treated slide in a volume of 100 µl (DMEM, 10% FCS, 100 IU/ml penicillin, 100 µg/ml streptomycin). Then 100 µg/ml or 1000 µg/ml Chitosan-NP or silica-NP are added with or without fluorescence for different time points in 100 µl cell culture medium. After the incubation phase the cells are scraped, washed twice with PBS and prepared for flow cytometry.

Experimental results are shown in FIGS. 1 and 2: Size dependent uptake of FITC-loaded NP or control NP without FITC-loading by myeloid antigen presenting cells (n=4 as triplicates). The mean±SD of all tested NP-sizes is shown for chitosan and silica for 0.1 mg/ml.

Besides chitosan, silica and PLGA nanoparticles (all FITC-labelled) have been studied to determine the preferred particle size for uptake by antigen presenting cells. Results for silica NP are also presented here because it is technically feasible to manufacture those particles also in the micrometer scale (on the contrary to chitosan particles). The results for chitosan NP (and silica) indicate that the uptake rate decreases with particle sizes above 500 nm. The sweet spot for particle size for favorable uptake by antigen-presenting cells appears to be 200-300 nm.

Immunologic Test Methods

Cell culture see above

Isolation of CD8+ T cells (CTLs)

Naive CD8+ T cells are isolated from spleen of OTI mice and purified by AUTOMACS (Miltenyi Biotec). After counting the cells they are directly used for in vitro co-culture with macrophages or dendritic cells.

Flow cytometry

Antibody staining is done in presence of Fc receptor blockade (monoclonal antibody 2.4G2 to mouse CD16-CD32 (10 µg/ml); prepared in-house) in flow cytometry buffer. A FACSCANTO II or FORTESSA (BD Biosciences) and FLOWJO sofware (TreeStar) are used for acquisition and data analysis. HOECHST 33258 (10 µg/ml; Sigma-Aldrich) is used for exclusion of dead cells. Antibodies used for flow cytometry were as follows (eBioscience): allophycocyanin- or ALEXA FLUOR 488-conjugated anti-CD69 (H1.2F3).

In Vitro Experiments

For the in vitro evaluation of chitosan-Ova-NP $5 \times 10^4$ macrophages or dendritic cells in a cell-culture-treated 96-well plate in a volume of 100 µl (DMEM, 10% FCS, 100 IU/ml penicillin, 100 µg/ml streptomycin) are used. Then $1 \times 10^5$ freshly isolated CD8$^+$ OTI T cells in 50 µl medium and chitosan-Ova-NP or free unloaded ovalbumin of the same concentration in 50 µl medium are added. After 24 h the supernatant, which was stored at −20° C. for subsequent ELISA measurements, is isolated and the remaining cells are used for flow cytometry analysis.

Cytokine Measurements

A mouse-specific ELISA for the detection of IL-2 (eBioscience) is used for the supernatants generated in vitro and the bead-based Th1/Th2 10plex (FlowCytomix, eBioscience) is used to determine T cell specific cytokines in serum of blood samples.

Experimental results are shown in FIG. 3: Comparison of differently deacetylated chitosan NP. Mean+/−SD of the antigen dependent CD69 expression of OTI t cells and IL-2 production. The NP size for chitosan is 250±30 nm. OTI t cells were incubated with the indicated Ovalbumin concentration either as unbound control (Ovalbumin panel) or loaded within NP of the indicated polymer type for 24 h. CD69 expression was detected by FACS, IL-2 by ELISA.

Nanoparticles (~260 nm) made of chitosans of different degrees of deacetylation (DD) are investigated for their in vitro performance in common immunological settings (CD69, IL-2) using ovalbumin as a model antigen. Chitosan nanoparticles with a DD of 75 or 95% show an increased immunological effect in comparison to soluble ovalbumin, by factor 10 in the case of IL-2. This improvement is within the expected range resulting from the combination of the adjuvant properties of nanoparticles and chitosan. Surprisingly the chitosan nanoparticles with a DD of 90% show a dramatic increase in immune response (factor 38 compared to soluble Ovalbumin for IL-2, see FIG. 3) in comparison to the same particles with DD of 75 or 95% which is in opposite to the prior art findings. The data demonstrate the superior immune response of the particles of the present invention compared to prior art formulations and their usefulness for therapeutic vaccination.

Preparation of Microparticles

To obtain a dry powder formulation, a matrix of 2% (w/V) mannitol(PEARLITOL 200 SD, Roquette, France) is added to the nanoparticle suspension and spray dried using the BÜCHI B-290 Mini spray dryer (Büchi, Flawil, Switzerland) at an inlet and outlet temperature of 80° C. and 35° C., respectively.

MMAD Analysis of Microparticles

Aerodynamical characterization using a Next Generation Impactor (NGI)

For the aerodynamical characterization HPMC capsules (size 3) are filled with 20 mg (±0.1 mg) of spray-dried powder. Capsules are dispersed by the Cyclohaler. The air flow rate is adjusted to a pressure drop of 4 kPa across the inhaler. The vacuum capacity is adjusted to 4 l flow for each inhalation. The different stages of the NGI are coated with a mixture of propylene glycol and isopropanol. One capsule is used for each run. After each run the NGI parts are cleaned with a defined amount of 0.1 M NaOH. The cleaning fluid is transferred to test tubes and incubated at 37° C. until a clear solution resulted. This solution is neutralized with 0.1 M HCl (1:1 ratio). The ovalbumin content is determined by BCA assay for each stage of the NGI. Based on the used flow rates, the fine powder fraction (FPF), the mass median aerodynamic diameter (MMAD) and the geometrical standard deviation (GSD) is calculated for the flow rate using the CITDAS software. Results are shown in FIG. 4: Deposition of Ovalbumin (OVA) out of the dry powder microparticle formulation in the NGI dispersed from Cyclohaler at 100 L/min (n=3, error bars show standard deviation). The FPF is 75.37% and the mass median aerodynamic diameter (MMAD) is 1.102 μm. This indicates a high fraction of particles capable for distribution in the lung.

Spray-dried microparticles were investigated on their ability to release OVA-loaded chitosan NP of the initial size upon dispersion in aqueous media. Results are shown in FIG. 5: original NP before SD (black line) size average 190.5 nm PDI 0.182; After SD (grey line) size average 209.5 nm PDI 0.145 (SD: Spray Drying, NP: Nanoparticles).

Particle size and polydispersity index of the original and treated NP are similar. This indicates that spray-drying does not alter the favorable target product profile of NP for vaccination.

Figure 1:
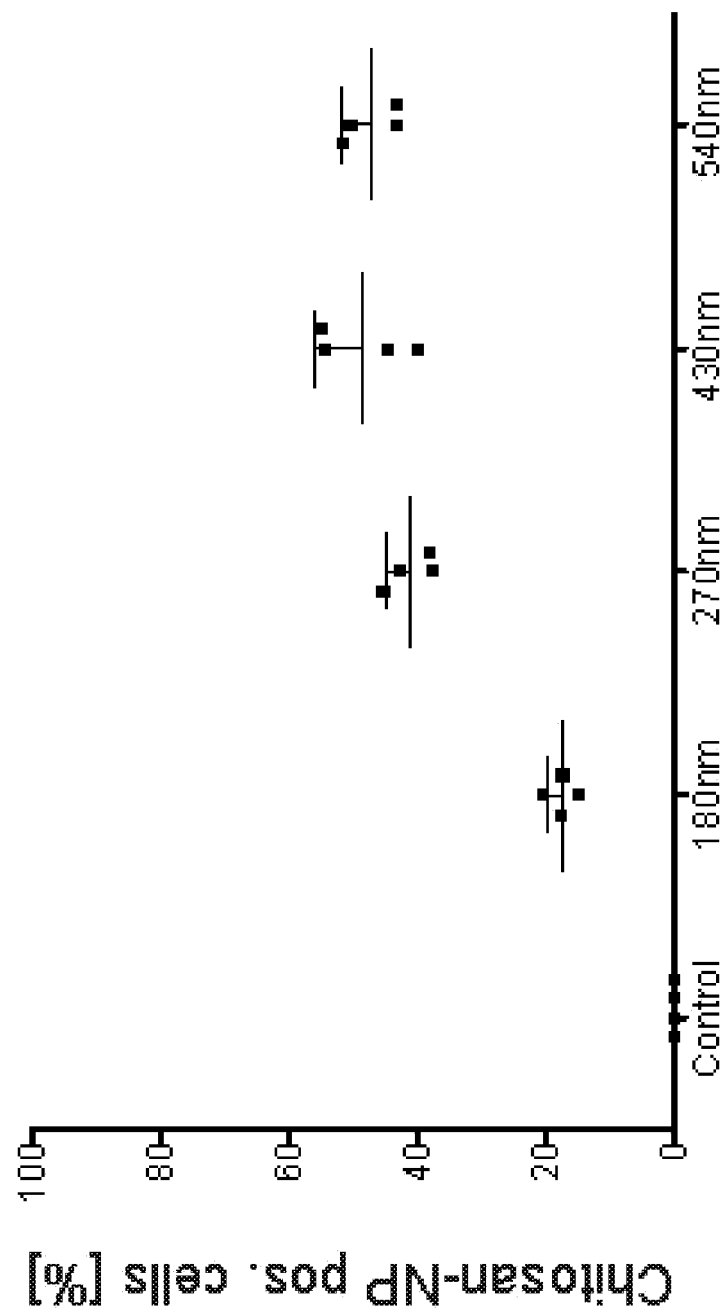
FIG. 1 is a graph.
Figure 2:
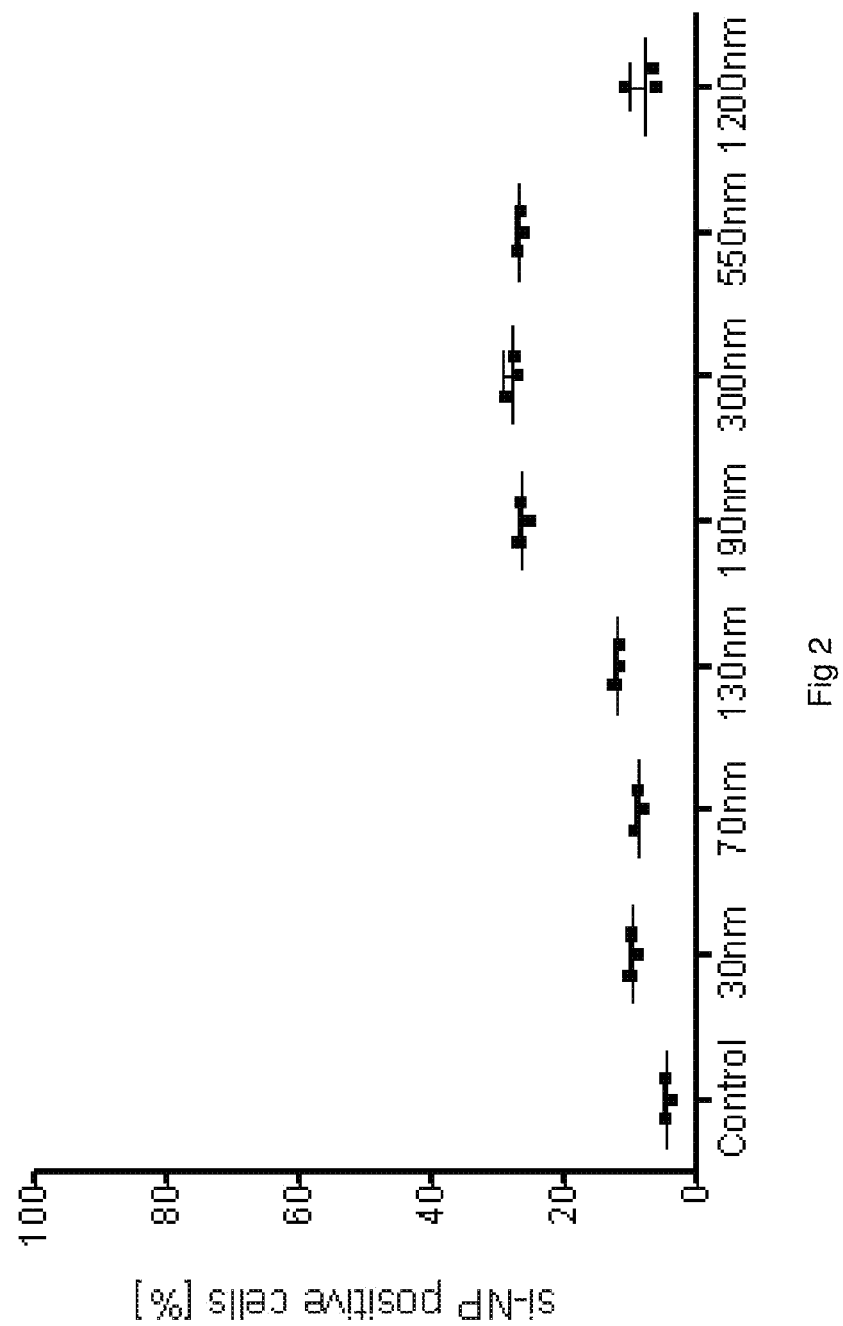
FIG. 2 is a graph.
Figure 3:
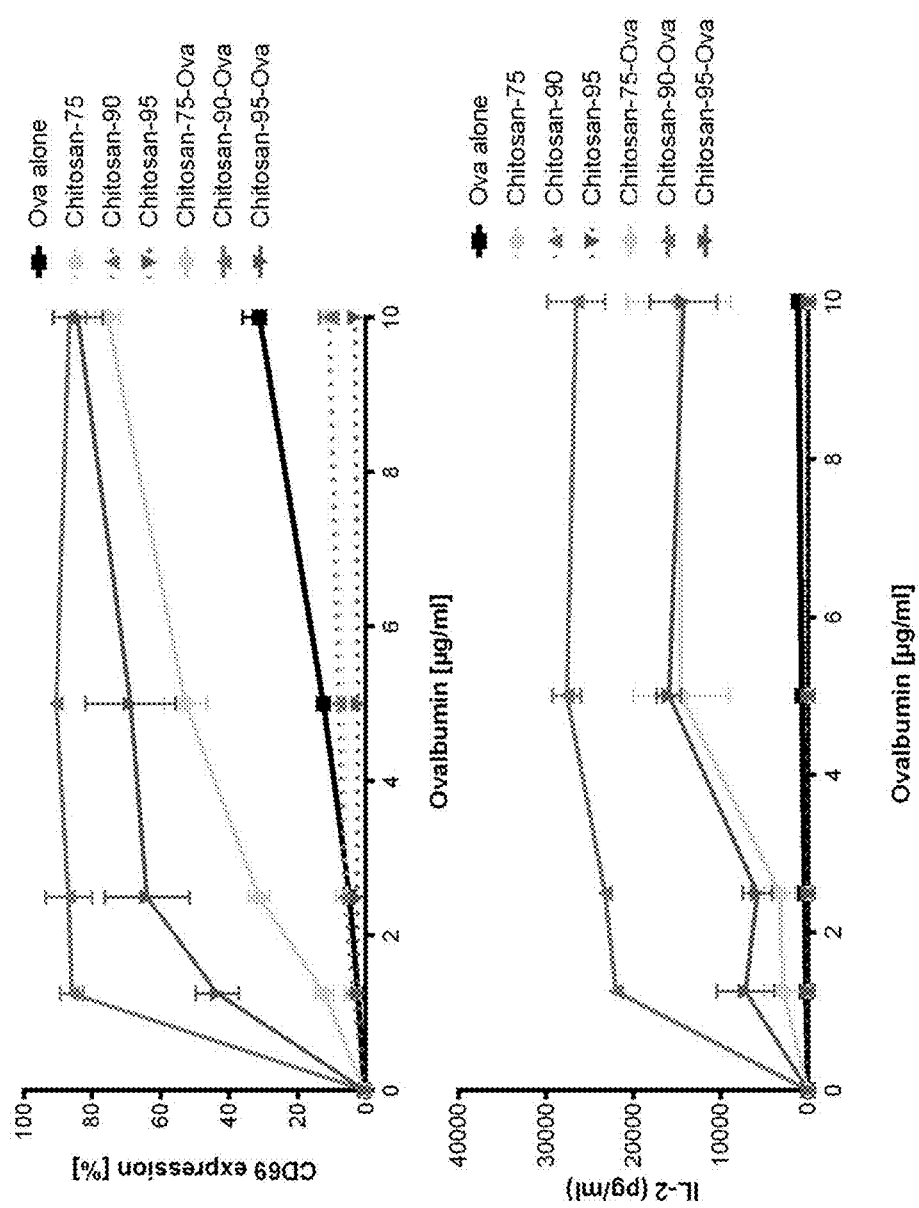
FIG. 3 is a graph.
Figure 4:
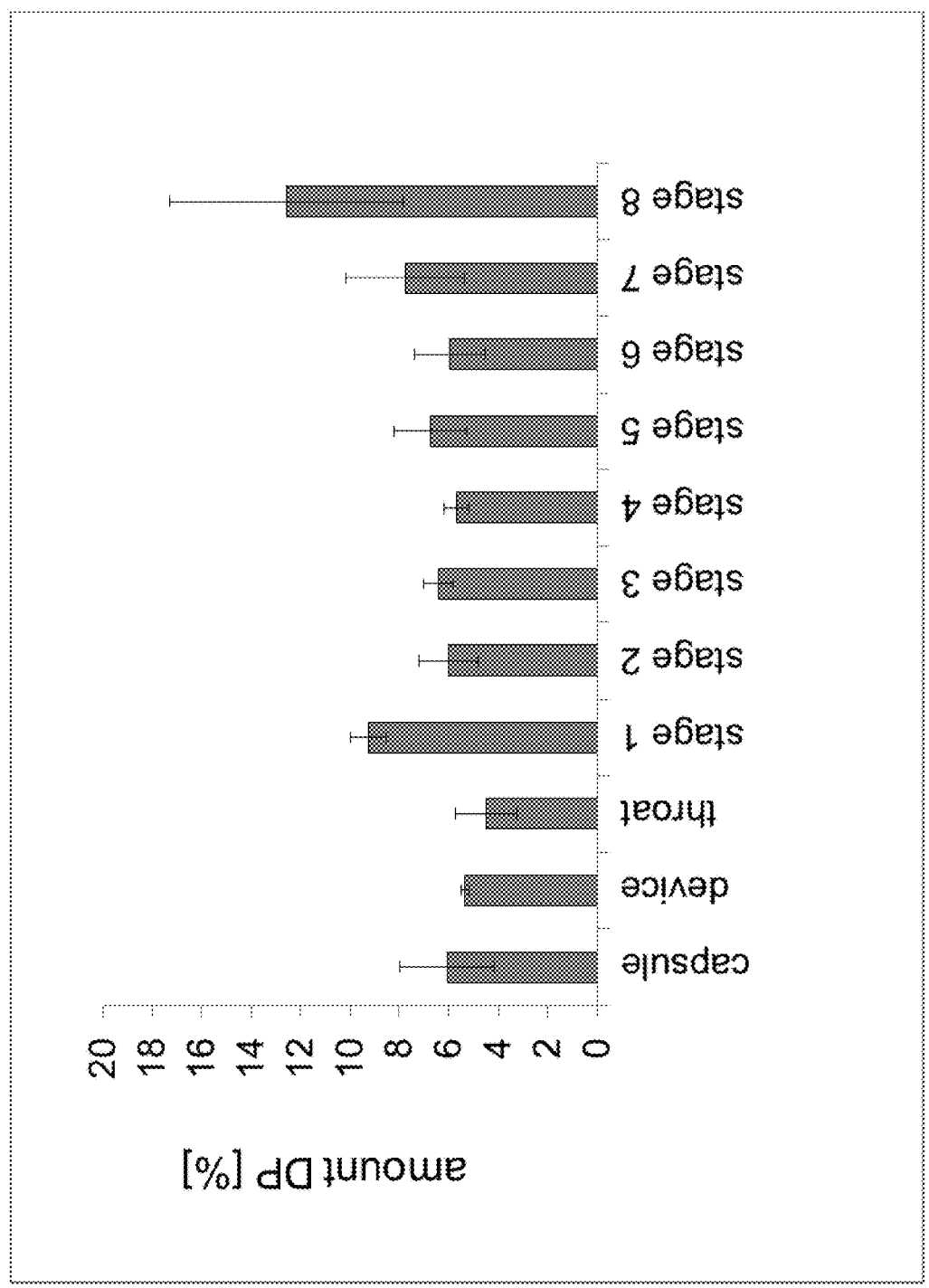
FIG. 4 is a graph.
Figure 5:
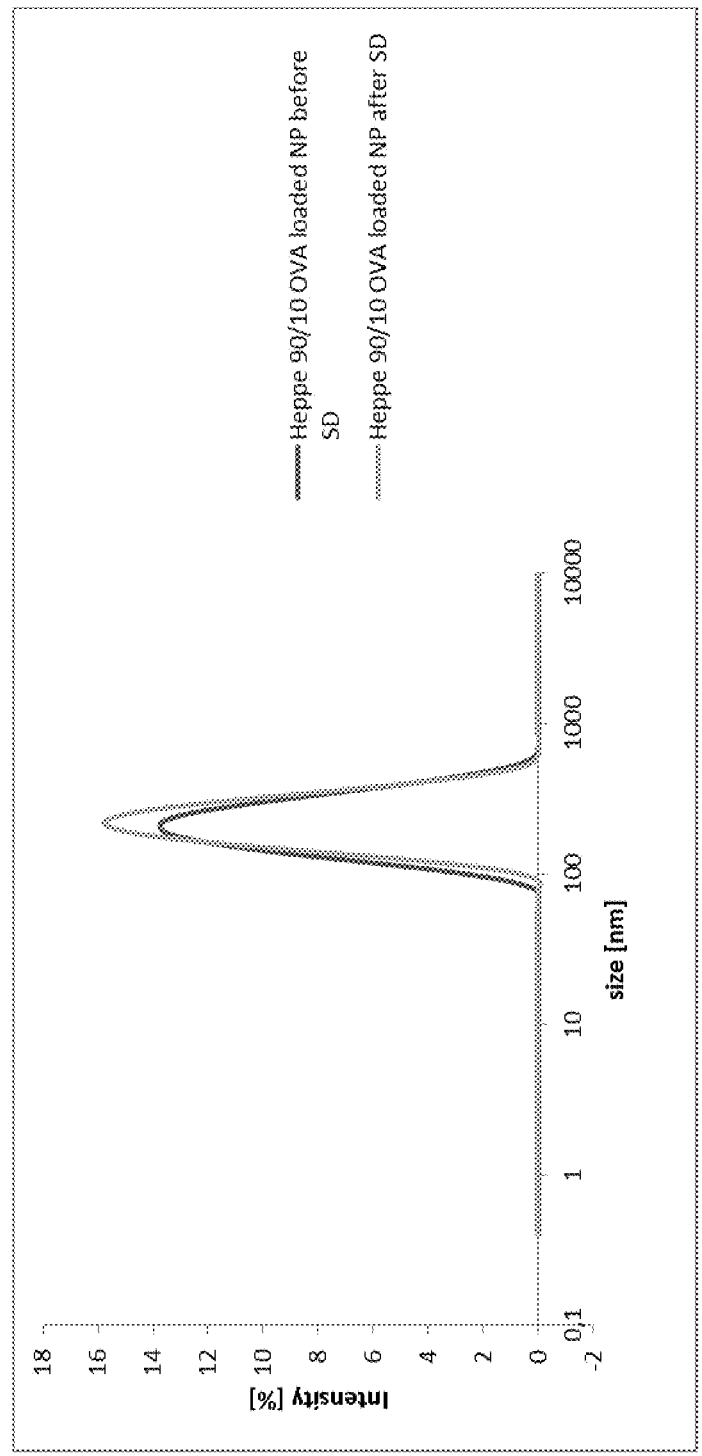
FIG. 5 is a graph.

The invention claimed is:

1. A nanoparticle comprising chitosan and an antigen, wherein the chitosan has a degree of deacetylation of about 90% and a molecular weight from 5 kDa to 80 kDa.

2. The nanoparticle according to claim 1, wherein the chitosan has a molecular weight from 10 kDa to 70 kDa.

3. The nanoparticle according to claim 1, wherein the nanoparticle has a mean size from 100 nm to 500 nm.

4. The nanoparticle according to claim 1, further comprising a counterion.

5. The nanoparticle according to claim 4, wherein the counterion is carboxymethylcellulose, pentasodium tripolyphosphate, sodium cholate, heparin, low MW hyaluronic acid, alginate, pectin, carrageenan or poly(acrylic acid).

6. The nanoparticle according to claim 1, wherein the antigen is a peptide, a protein or a nucleic acid.

7. The nanoparticle according to claim 1, further comprising an adjuvant.

8. A vaccine comprising the nanoparticle according to claim 1.

9. A method of treatment comprising administering the nanoparticle according to claim 1 by therapeutic vaccination.

10. The method according to claim 9 wherein the nanoparticle is administrated by mucosal administration or by parenteral injection.

11. The method according to claim 10, wherein the mucosal administration is pulmonal or nasal administration.

12. A process for the preparation of the nanoparticle according to claim 1, wherein the nanoparticle is prepared by ionic gelation.

13. The process according to claim 12 comprising; (a) preparing an aqueous solution comprising chitosan and an antigen; (b) preparing an aqueous solution comprising a counterion; (c) mixing the aqueous solution prepared in step (a) and the aqueous solution prepared by step (b); (d) stirring the mixture obtained in step (c) to produce an aqueous dispersion containing chitosan nanoparticles; (e) collecting the nanoparticles obtained in step (d).

14. The process according to claim 13, wherein step (c) is performed by addition of the aqueous solution prepared in step (b) to the aqueous solution prepared by step (a).

15. A microparticle comprising the nanoparticle according to claim 1 and a matrix agent.

16. The microparticle according to claim 15, wherein the matrix agent is a monosaccharide, a disaccharide, a sugar alcohol or a polysaccharide.

17. The microparticle according to claim 16, wherein the matrix agent monosaccharide is glucose, the matrix agent disaccharide is trehalose, sucrose or lactose, the matrix agent sugar alcohol is mannitol or sorbitol, and the matrix agent polysaccharide is starch or dextrane.

18. The microparticle according to claim 15, wherein the microparticle has a mass median aerodynamic diameter from 0.5 μm to 5 μm.

19. A vaccine comprising the microparticle according to claim 15.

20. A method of treatment comprising administering a microparticle according to claim 15 for therapeutic vaccination.

21. The method according to claim 20, wherein the microparticle is administrated by mucosal administration.

22. The method according to claim 21, wherein the mucosal administration is pulmonal or nasal administration.

23. A process for the preparation of a microparticle comprising spray drying a liquid containing the nanoparticle according to claim 1 and a matrix agent.

24. The process according to claim 23, comprising:
(a) preparing an aqueous dispersion comprising the nanoparticle and the matrix agent being dissolved therein;
(b) spray-drying the aqueous dispersion prepared in step (a) to produce nanoparticle-containing microparticle;
(c) collecting the microparticle obtained in step (b).

25. The nanoparticle according to claim 3, wherein the nanoparticle has a mean size from 200 nm to 400 nm.

26. The nanoparticle according to claim 25, wherein the nanoparticle has a mean size from 200 nm to 300 nm.

27. The microparticle according to claim 18, wherein the microparticle has a mass median aerodynamic diameter from 2 µm to 5 µm.

28. The nanoparticle according to claim 2, wherein the chitosan has a molecular weight from 25 kDa to 50 kDa.

* * * * *